(12) United States Patent
Panigrahi et al.

(10) Patent No.: US 11,443,421 B2
(45) Date of Patent: Sep. 13, 2022

(54) METHOD AND SYSTEM FOR DETECTING INFESTATION IN AGRICULTURAL PRODUCTS

(71) Applicant: Wipro Limited, Bangalore (IN)

(72) Inventors: Sarthak Panigrahi, Bangalore (IN); Anandaraj Thangappan, Bangalore (IN)

(73) Assignee: Wipro Limited, Bangalore (IN)

( * ) Notice: Subject to any disclaimer, the term of this patent is extended or adjusted under 35 U.S.C. 154(b) by 0 days.

(21) Appl. No.: 17/186,252

(22) Filed: Feb. 26, 2021

(65) Prior Publication Data

US 2022/0222798 A1 Jul. 14, 2022

(30) Foreign Application Priority Data

Jan. 12, 2021 (IN) .............................. 202141001475

(51) Int. Cl.
*G06T 7/00* (2017.01)
*G06K 9/62* (2022.01)
(Continued)

(52) U.S. Cl.
CPC .............. *G06T 7/001* (2013.01); *G01B 11/22* (2013.01); *G01N 23/04* (2013.01); *G01N 23/083* (2013.01); *G01N 33/025* (2013.01); *G01S 17/89* (2013.01); *G06K 9/6201* (2013.01); *G06K 9/627* (2013.01); *G06K 9/6217* (2013.01); *G06K 9/6288* (2013.01); *G06V 10/60* (2022.01); *G01N 2223/04* (2013.01); *G01N 2223/40* (2013.01); *G01N 2223/618* (2013.01); *G01N 2223/646* (2013.01); *G06T 2207/10028* (2013.01); *G06T 2207/10036* (2013.01); *G06T 2207/10116* (2013.01); *G06T 2207/30128* (2013.01); *G06V 10/58* (2022.01)

(58) Field of Classification Search
None
See application file for complete search history.

(56) References Cited

U.S. PATENT DOCUMENTS 7,817,833 B2 10/2010 Ramsay et al.
8,290,305 B2 10/2012 Minear et al.
(Continued)

*Primary Examiner* — David Perlman
(74) *Attorney, Agent, or Firm* — Finnegan, Henderson, Farabow, Garrett & Dunner, LLP

(57) ABSTRACT

System and method of detecting infestation in agricultural products is disclosed. In one embodiment, an infestation detection system captures hyperspectral imaging data and depth imaging data for a plurality of points on an agricultural product upon directing a light source at the agricultural product. The system analyses the captured imaging data to derive morphological details as well as spectral signatures for complete 360° view of the plurality of points on the agricultural product. In an embodiment, the spectral signatures may be corrected for one or more pixels associated with the plurality of points in the agricultural product by integrating the hyperspectral imaging data with the depth imaging data. The system further classifies one or more regions of the agricultural product based on matching of spectral signatures for the one or more pixels with pre-defined spectral signatures stored for a plurality of agricultural products, and accordingly detect infestation.

17 Claims, 6 Drawing Sheets

(51) Int. Cl.
*G01N 23/04* (2018.01)
*G01B 11/22* (2006.01)
*G01S 17/89* (2020.01)
*G01N 23/083* (2018.01)
*G01N 33/02* (2006.01)
*G06V 10/60* (2022.01)
*G06V 10/58* (2022.01)

(56) References Cited

U.S. PATENT DOCUMENTS

| | | |
|---|---|---|
| 9,410,888 B2 | 8/2016 | Jayasooriya et al. |
| 9,448,110 B2 | 9/2016 | Wong |
| 10,197,504 B2 | 2/2019 | Sahu et al. |
| 2014/0118555 A1 | 5/2014 | Hegg et al. |
| 2018/0113083 A1* | 4/2018 | Van Dael ............... G01N 23/18 |
| 2018/0365822 A1* | 12/2018 | Nipe ..................... G06V 10/40 |
| 2019/0064363 A1 | 2/2019 | Redden et al. |
| 2020/0037596 A1 | 2/2020 | Peters et al. |
| 2020/0111053 A1* | 4/2020 | Bogolea ............... G06V 10/143 |

* cited by examiner

METHOD AND SYSTEM FOR DETECTING INFESTATION IN AGRICULTURAL PRODUCTS

TECHNICAL FIELD

This disclosure relates generally to inspection of agricultural products, and more particularly to a system and a method of detecting infestation in agricultural products.

BACKGROUND

Reliable and accurate detection and identification of disease and damages in agricultural crops and plants is always a challenge in food industry. Plant disease identification is significant activity in the processing and packaging of agricultural products. Post harvesting, the handling and processing of an agricultural product is very crucial for the life of product, especially while detecting damages due to environmental stress, insects, pests, pathogens etc. Early detection of stress symptoms and infestation in the agricultural products would be beneficial to the farmers and growers to provide treatment at early stages and to segregate good quality products from damaged products. For example, if pathogens or insect-eggs remain undetected, it may grow with ripening of products, and can adversely affect the quality and commercial value of the harvested agricultural products such as fruits. Thus, it is essential to detect the infestation in the agricultural at early stages, which might not be visible from outside. The collected agricultural products are tested and assessed before being packed for exporting and transportation.

Existing methods which are used for assessing agricultural products include visual inspection, laboratory analysis and the like. However, such techniques requires manual handling of the products which can affect the product quality. In some cases, the inspection expert may collect samples of products for in-depth analysis and screening of whole batch of agricultural products. Such sample-based analysis is not fool-proof and causes permanent destruction of product samples. To address this, some non-destructive techniques are known such as RGB camera based image analysis, Hyper Spectral Imaging (HSI) for proper data capture and analysis of damages in product samples. However, the infestation may be present at inner region of the agricultural products which still remain undetected, and may cause the growth of infestation resulting in the passing of infestation to other agricultural products packed together. In some cases where the infestation at certain regions of products remain undetected due to its shape and size, and if the product is not assessed thoroughly, it results in inaccurate and incomplete results. Such detection techniques, even if detect infestation but not accurately for each and every product, may result in cancelling of complete batch of products due to infested products. Therefore, more accurate and thorough inspection of agricultural products is required to detect infestation.

The information disclosed in this background of the disclosure section is only for enhancement of understanding of the general background of the invention and should not be taken as an acknowledgement or any form of suggestion that this information forms the prior art already known to a person skilled in the art.

SUMMARY

In one embodiment, a method of detecting infestation in agricultural products is disclosed. The method includes capturing hyperspectral imaging data and depth imaging data for a plurality of points on an agricultural product upon directing a light source at the plurality of points on the agricultural product. The method further includes deriving morphological details for the plurality of points on the agricultural product. The method further includes determining spectral signatures for one or more pixels associated with the plurality of points in the agricultural product for complete 360° view by integrating the hyperspectral imaging data with the depth imaging data. The method further includes classifying one or more regions of the agricultural product based on matching of the spectral signatures determined for the one or more pixels with pre-defined spectral signatures stored for a plurality of agricultural products in an infestation knowledge database, and thereby detecting the infestation in the agricultural product.

In one embodiment, an infestation detection system for agricultural products is disclosed. In one example, the infestation detection system includes a plurality of image sensors, at least one processor and a memory communicatively coupled to the at least one processor. The memory stores the at least one processor-executable instructions, which, on execution, causes the at least one processor to capture hyperspectral imaging data and depth imaging data for a plurality of points on an agricultural product upon directing a light source at the plurality of points on the agricultural product. The processor-executable instructions, on execution, may further cause the at least one processor to derive morphological details for the plurality of points on the agricultural product. The processor-executable instructions, on execution, may further cause the at least one processor to determine spectral signatures for one or more pixels associated with the plurality of points in the agricultural product for complete 360° view by integrating the hyperspectral imaging data with the depth imaging data. The processor-executable instructions, on execution, may further cause the at least one processor to classify one or more regions of the agricultural product based on matching of spectral signatures determined for the one or more pixels with pre-defined spectral signatures stored for a plurality of agricultural products in an infestation knowledge database, and thereby detecting infestation in the agricultural product.

In yet another embodiment, a non-transitory computer-readable medium storing computer-executable instruction for detecting infestation in agricultural products is disclosed. In one example, the stored instructions, when executed by a processor, may cause the processor to perform operations including capturing hyperspectral imaging data and depth imaging data for a plurality of points on an agricultural product upon directing a light source at the plurality of points on the agricultural product. The operations may further include deriving morphological details for the plurality of points on the agricultural product. The operations may further include determining spectral signatures for one or more pixels associated with the plurality of points in the agricultural product for complete 360° view by integrating the hyperspectral imaging data with the depth imaging data. The operations may further include classifying one or more regions of the agricultural product based on matching of the spectral signatures determined for the one or more pixels with pre-defined spectral signatures stored for a plurality of agricultural products in an infestation knowledge database, and thereby detecting the infestation in the agricultural product.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present invention relates to a method and a system for detecting infestation in agricultural products. The method and system provides complete 360° view analysis of one or more agricultural products post-harvesting. The method and system includes capturing imaging data for a plurality of points on an agricultural product from a plurality of image sensors including Hyper Spectral Imaging (HSI) spectrometers and depth sensors, for example LIDAR (Light Detection and Ranging), with the help of a light source. The imaging data includes hyperspectral images of the plurality of points for complete 360° view of the agricultural product captured upon rotating entire surface of the agricultural product up to 360° angle. The hyperspectral images may be used to derive morphological details as well as spectral signatures of the agricultural product by using depth information captured by the depth sensors. The proposed method and system may compute a transformation function by integrating the hyperspectral imaging (HSI) data with the depth imaging data for the plurality of points based on change in intensity over change in angle between a first point at top plane of the agricultural product to a second point at any region other than the top plane of the agricultural product. Herein, the transformation function indicates loss in spectrum for the one or more pixels due to spatial position of the plurality of points in the agricultural product. According to the proposed method, the computed transformation function may be used in correcting loss in spectrum for one or more pixels associated with the plurality of points in the agricultural product based on depth information i.e. captured using depth sensors, associated with the one or more pixels in the agricultural product. The proposed method and system classifies one or more regions of the agricultural product based on matching of the spectral signatures determined for the one or more pixels with pre-defined spectral signatures stored for a plurality of agricultural products, and accordingly detect infestation in the agricultural product. In addition to that, the proposed system may utilize x-ray based penetrating data to identify infestation, if any, at inner region of the agricultural product.

Figure 1:
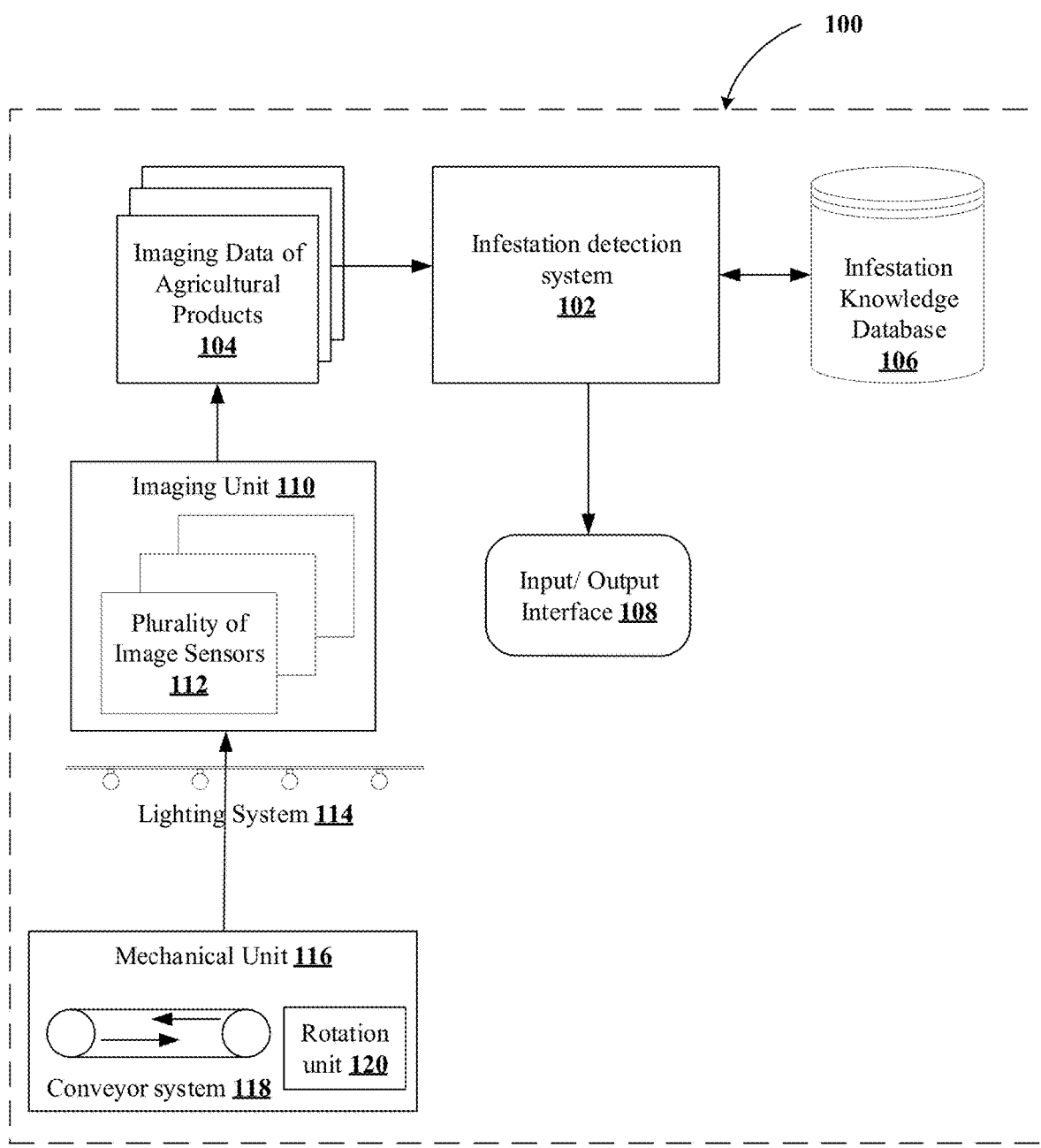
FIG. 1 illustrates an exemplary environment for detecting infestation in an agricultural product, in accordance with some embodiments of the present disclosure.

FIG. 1 illustrates a block diagram of an exemplary environment for detecting infestation in one or more agricultural products in accordance with some embodiments of the present disclosure. As shown in FIG. 1, the exemplary environment 100 may include a production site and/or logistics department, where harvested agricultural products are stored or packed for transportation. In an embodiment, the agricultural products may include wide range of macroscopic food products including, but not limited to, fruits of various shapes and sizes. In an embodiment, various types of infestation in the one or more products may be identified using the infestation detection system 102 configured at the environment 100.

In an embodiment, the infestation detection system 102 may be any computing system capable of analyzing the imaging data of the one or more agricultural products 104 and detecting the infestation in accordance with various embodiments of the claimed invention. As an example, the infestation detection system 102 may include, without limiting to, a desktop computer, a laptop, a smartphone or even a server computer. In an implementation, the infestation detection system 102 may be configured at the environment 100 and locally operated at the logistics/production site. In an alternative implementation, the infestation detection system 102 may be configured and operated from a remote location and the imaging data associated with the one or more agricultural products 104 may be transmitted to the infestation detection system 102 over a wired and/or wireless communication channel. Further, the infestation detection system 102 may be coupled with an infestation knowledge database 106 for retrieving information such as, without limitation, spectral signatures and/or corrected spectrum data of the one or more agricultural products, morphological details of the agricultural products and the like, which are required for detecting infestation in the one or more agricultural products 104. In an embodiment, the infestation detection system 102 and the infestation knowledge database 106 may be connected over a wired and/or wireless communication channel. The infestation information and/or classification of the agricultural product may be provided to an executive or an inspector detecting infestation in real-time via a display 108.

In an embodiment, the exemplary environment 100 may further include a mechanical unit 116, and an imaging unit 110 to obtain imaging data associated with an agricultural product that can be used by the infestation detection system 102 to detect infestation in the agricultural product. The imaging unit 110 may include a plurality of image sensors 112 and a lighting system 114 to capture a plurality of images obtained using the plurality of image sensors 112 in order to perform image analysis of the one or more agricultural products 104. In an embodiment, the mechanical unit 116 may include mechanical components such as conveyor system 118 which may work in conjunction with a rotation unit 120 to perform rotation operation on each of the one or more agricultural products 104 along with other components for cleaning and grading of the agricultural products. The infestation detection system 102 may detect infestation based on imaging data generated by the imaging unit 110, and provide details of infestation such as type of infestation, region of infestation, stages of infestation, quality of agricultural products, life of agricultural products and the like.

In an embodiment, the infestation detection system 102 may analyze the captured imaging data including, but not limited to, hyperspectral imaging data, depth imaging data and the like, obtained from the imaging unit 110. In some embodiments, the imaging data may include spectral information associated with a plurality of points on the each of the one or more agricultural products 104. Herein the spectral information may include spectral signatures obtained by the imaging unit 110 for the plurality of points from the hyperspectral imaging data as will be explained further in below paragraphs. Further, the infestation detection system 102 may determine loss in spectrum for the plurality of points based on the depth imaging data captured by the imaging unit 110. In an embodiment, such loss in spectrum is required to rectify loss of reflectance in the imaging data, determine infestation accurately in each of the one or more agricultural products 104 and classify the one or more agricultural products 104 based on infestation for its quality, as will be explained below in conjunction with FIG. 2.

Figure 2:
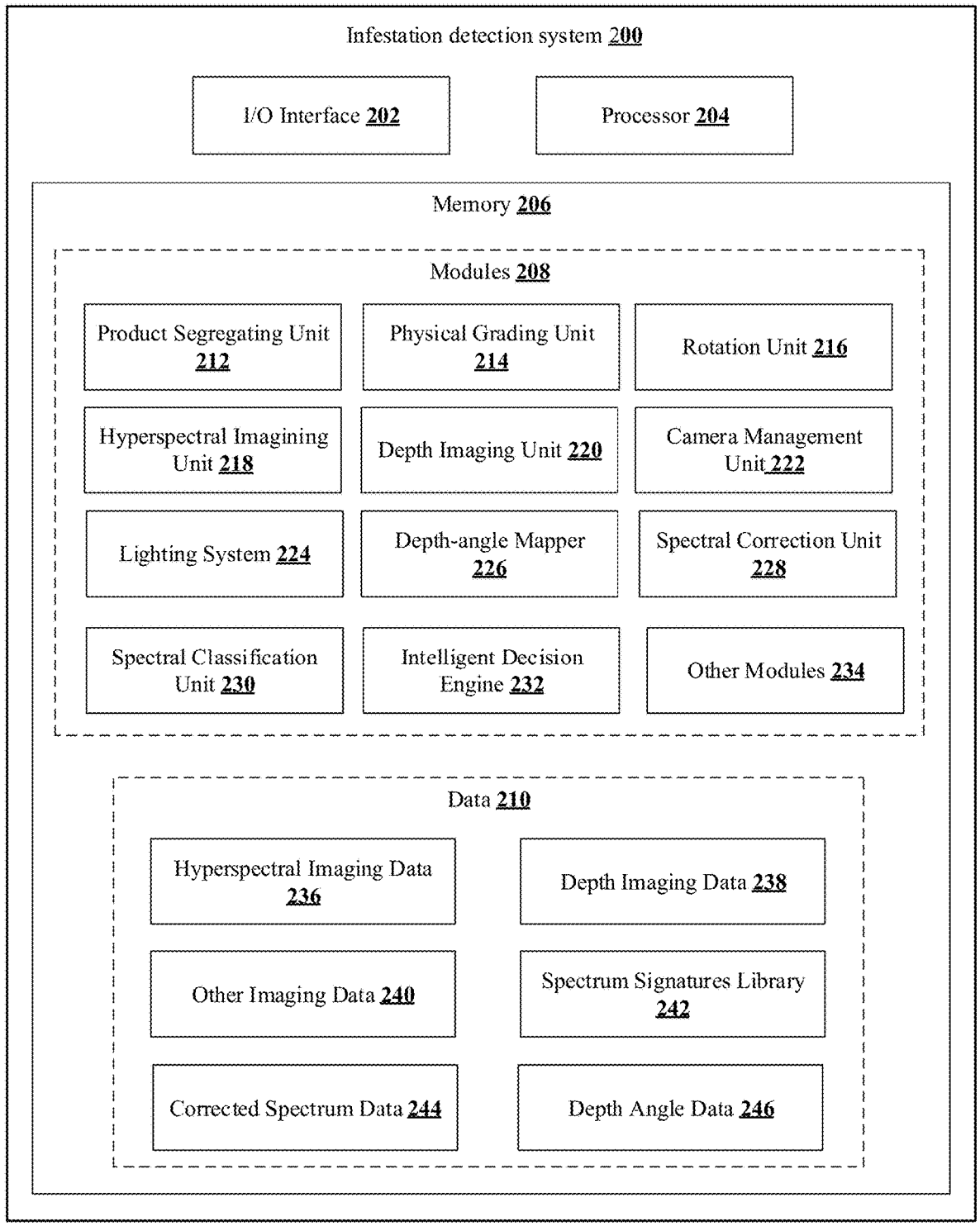
FIG. 2 is a block diagram illustrating components of an infestation detection system in accordance with some embodiments of the present disclosure.

Referring now to FIG. 2, a block diagram of an infestation detection system 200 is illustrated, in accordance with some embodiments of the present disclosure. In particular, the infestation detection system 200 may include at least one processor 204 and a memory 206. The memory 206 of the infestation detection system 200 may include various modules 208, that may store the instructions that, when executed by the at least one processor 204, cause the at least one processor 204 to perform various functions in order to detect infestation in an agricultural product, in accordance with aspects of the present disclosure. In some embodiments, the infestation detection system 200 may include product segregating unit 212, physical grading unit 214, rotation unit 216, hyperspectral imagining unit 218, depth imaging unit 220, camera management unit 222, lighting system 224, depth-angle mapper 226, spectral correction unit 228, spectral classification unit 230, intelligent decision engine 232, and other modules 234. The infestation detection system 200 may be communicatively coupled with an infestation knowledge database (not shown in FIG. 2), which may store the morphological details and the spectral signatures associated with the one or more pixels in the agricultural product. In some embodiments, the infestation knowledge database may reside in the memory 206 of the infestation detection system 200. Further, in some embodiments, the infestation detection system 200 may store various data 210 in the memory 206. For example, hyperspectral imaging data 236, depth imaging data 238, other imaging data 240, spectral signatures library 242 associated with the agricultural product, corrected spectrum data 244 computed for the agricultural product, depth angle data 246, and other types of data may be stored as data 210. In an embodiment the spectral signatures library 242 and the corrected spectrum data 244 may be stored in the infestation knowledge database (not shown in FIG. 2). The infestation detection system 200 may provide detected infestation results to an operator with the help of an Input/Output (I/O) interface 202. As will be appreciated by those skilled in the art, all such aforementioned modules and data 212-246 may be represented as a single module or a combination of different modules. Moreover, as will be appreciated by those skilled in the art, each of the modules and databases 212-246 may reside, in whole or in parts, on one device or multiple devices in communication with each other.

In an embodiment, the infestation detection system 200 may be communicatively connected with a mechanical unit 116 (as shown in FIG. 1) which may include, but not limited to, a product segregation unit 212, a physical grading unit 214, and a rotation unit 216. In an embodiment, the product segregation unit 212 may include a cleaning unit (not shown in FIG. 2) that may clean the one or more agricultural products with water or brine solution and dry them using an air cannon or a blower. In another embodiment, the product segregation unit 212 may sort or group the one or more agricultural products 104 based on size or shapes to create batches of the one or more agricultural products with similar dimensions. In an embodiment, the product segregation unit 212 may allow the operators to initially segregate the one or more agricultural products 104 into good or bad ones to enhance decision making process implemented by the infestation detection system 200. In an embodiment, the rotation unit 216 may rotate each of the one or more agricultural products 104 batched together at 360° angle to enable the imaging unit to capture complete 360° view of the each of the one or more agricultural products 104. In an embodiment, the rotation unit 216 may synchronize with the imaging unit 110 so that the infestation detection system 200 may properly capture imaging data for various regions on the one or more agricultural products 104 in one time. It is known to person skilled in the art that either the lighting system 224 can be moved or multiple imaging systems may be used in order to capture the entire surface of the one or more agricultural products 104.

In an embodiment, the imaging unit 110 conducts an analysis on the plurality of images from the imaging data captured for the one or more agricultural products 104 using the plurality of image sensors 112 and lighting system 114. The plurality of image sensors 112 may include Hyperspectral Imaging Unit (HSI unit) 218, Depth Imaging unit 220, X-ray or CT (Computed Tomography) imaging unit, and the like. The HSI unit 218 may include a HSI camera that captures spectrum data in the visible and Near-Infrared (NIR) regions of one or more points associated with each of the one or more agricultural products 104. The Depth Imaging unit 220 includes depth sensors such as LIDAR sensors that are responsible for capturing the depths at various levels of each of the one or more agricultural products 104 and generate point cloud image for the agricultural product during inspection. In addition to that, an X-ray scanner having penetrating imaging capabilities may be used to acquire feature details specific to inner regions of the agricultural product being inspected. In an embodiment, the lighting system 114 includes light source required to properly capture the imaging data by the plurality of image sensors 112. As the HSI data 236 largely depends on the transmittance and reflectance characteristics of an object being analyzed, the light source is required to be in accordance with the wavelength region being captured by the imaging unit 110. Similarly, other image sensors may have specific lighting requirements for uniform spread of light intensity or luminance over the entire surface of the one or more agricultural products 104.

In an embodiment, the imaging unit 110 may include a camera management unit 222 for capturing the plurality of images in different modalities such as HSI data, depth data, x-ray data and the like for each of the one or more agricultural products 104. The camera management unit 222 is configured to synchronize each of the plurality of image sensors 112 to capture different modalities in such a way that every pixel in one modality corresponds to the same pixel in all other modalities, in a common coordinate system. This imaging unit 110 may be synchronized with the conveyor system 118 with the help of the rotation unit 120 such that the speed of modalities are mechanically calibrated to coordinate the speed of conveyor belt with a modality-specific capturing region for capturing the plurality of images using one or more image sensors installed in the setup.

In an embodiment, the infestation detection system 200 may take input from the imaging unit 110 in order to provide decision related to infestation in the one or more agricultural products 104. The infestation detection system 200 may include an infestation knowledge database 106 for storing the set of spectral signatures associated with the one or more points in the spectral signatures library 242 for various physical classes of the one or more agricultural products 104. In addition to that, the infestation knowledge database 106 may store corrected spectrum data 244 determined based on fusion of the imaging data captured using the plurality of image sensors 112. For example, the corrected spectrum data 244 may use depth imaging data 238 as well as depth-angle data 246 for generating angles for a plurality of pixels in the agricultural product with respect to the top plane of the agricultural product. In some embodiments, the infestation knowledge database 106 may store the transformation function computed for the agricultural product based on fusion of the imaging data i.e. HSI data 236 and depth imaging data 238. In some embodiments, the infestation knowledge database 106 may also store a pre-computed transformation function, which is computed for correction in spectrum data for the one or more pixels specific to various classes of the one or more agricultural products 104.

The infestation detection system 200 may further include a depth angle mapper 226 which generates depth-angle values associated with the plurality of pixels of the agricultural product with respect to the top plane of the agricultural product. The depth-angle mapper 226 may utilizes the depth imaging data 238 captured using depth sensors to generate depth-angle values by using slope of the one or more points on the agricultural product that can be mapped with the HSI data 236 associated with the agricultural product for deriving the transformation function for correction in the spectrum.

In an embodiment, the infestation detection system 200 may include a spectral correction unit 228 which may create a customized spectral signatures library 242 for various classes of the one or more agricultural products 104 in order to detect infestation in real-time. The spectral signatures library 242 provides the spectral signatures which are used to classify the agricultural product based on damage and infestation. The spectral correction unit 228 utilizes the spectral signatures library 242 based on which spectral signatures obtained for each of the plurality of pixels may be corrected as a function of angle of reflection, resulting due to specific morphological features of the agricultural product such as slope, curve, edge and the like. The corrected spectral signatures are stored in the infestation knowledge database 106, which may be used by the spectral classification unit 230 later for classification of the one or more agricultural products 104.

Furthermore, the infestation detection system 200 may further include an Intelligent Decision Engine 232 which takes input the imaging data captured for the each of the plurality of pixels of the agricultural product, and the spectral signatures library 242 as well as corrected spectrum data 244 stored in infestation knowledge database 106 for infestation detection.

In an embodiment, the infestation detection system 200 may analyze the spectral signatures associated with the agricultural product captured in the form of a hypercube of the agricultural product, which is divided into plurality of data-cubes containing spectral signatures for each of the plurality of pixels of the agricultural product. In the embodiment, the intelligent decision engine 232 may analyze one or more of plurality of data-cubes covering various morphological regions of the agricultural product and provide result as to whether the agricultural product has infestation or not. In some embodiments, the agricultural product may be identified as fresh, damaged or severely damaged. In an embodiment, the intelligent decision engine 232 may use a common discretionary threshold being set for various infestation levels in the agricultural product.

In some embodiments, the infestation knowledge database 106 may store the details regarding the morphological classes and respective spectral signatures for the one or more agricultural products 104. In such case, the intelligent decision engine 232 may consider the morphological details associated with the agricultural product as input to provide faster detection of infestation in the agricultural product.

Figure 5:
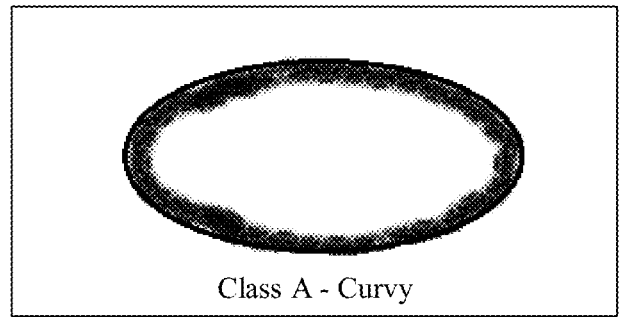
FIG. 5 illustrates an embodiment of an infestation detection system having morphological segmentation details associated with a plurality of agricultural products, in accordance with some embodiments of the present disclosure.
Figure 5:
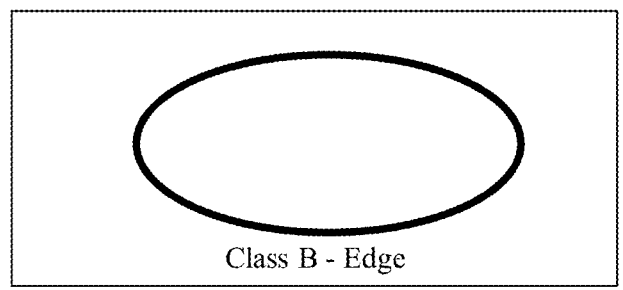
Figure 5:
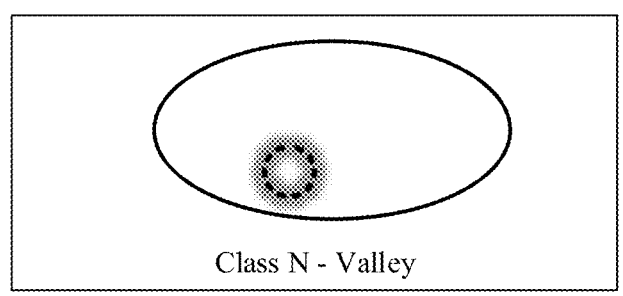

In some embodiments, the infestation detection system 102 having pre-defined morphological segmentation details associated with a plurality of agricultural products may implement machine learning technique wherein pre-trained data based on the imaging data from the plurality of sensors may be integrated to provide correct spectral signatures for the plurality of points associated with the agricultural product. The pre-trained machine learning model is trained with the depth imaging data 238 and the spectral signatures associated with the one or more morphological regions for the plurality of agricultural products. The imaging data may include HSI data 236 based on which a hypercube is created dividing the agricultural product into N data-cubes. In an embodiment, various regions of morphological segments extracted from the depth imaging data 238 may be used to divide the hypercube into N data-cubes. The morphological segments may include, but not limited to, curvy, edges, and valleys regions in the agricultural product as shown in FIG. 5.

Each morphological details will exhibit a different spectral signature for each physical class (such as infested, fresh and the like) along with the signature that it would have shown in an ideal scenario with no loss in spectrum. Accordingly, the infestation detection system 102 may classify each of the N data-cubes using the spectral signatures pre-defined for the morphological segments such as infested, fresh and the like. Based on classification, the intelligent decision engine 232 may use the pre-defined morphological segmentation details along with pre-stored spectral signatures and may quickly provide results for infestation detection for the agricultural product, when there is no need to make correction in the spectrum, in accordance with the embodiment.

It should be noted that the infestation detection system 102 may be implemented in programmable hardware devices such as programmable gate arrays, programmable array logic, programmable logic devices, and so forth. Alternatively, the infestation detection system 102 may be implemented in software for execution by various types of processors. An identified module of executable code may, for instance, include one or more physical or logical blocks of computer instructions which may, for instance, be organized as an object, procedure, function, or other construct. Nevertheless, the executables of an identified module need not be physically located together but may include disparate instructions stored in different locations which, when joined logically together, include the module and achieve the stated purpose of the module. Indeed, a module of executable code could be a single instruction, or many instructions, and may even be distributed over several different code segments, among different applications, and across several memory devices.

Figure 3:
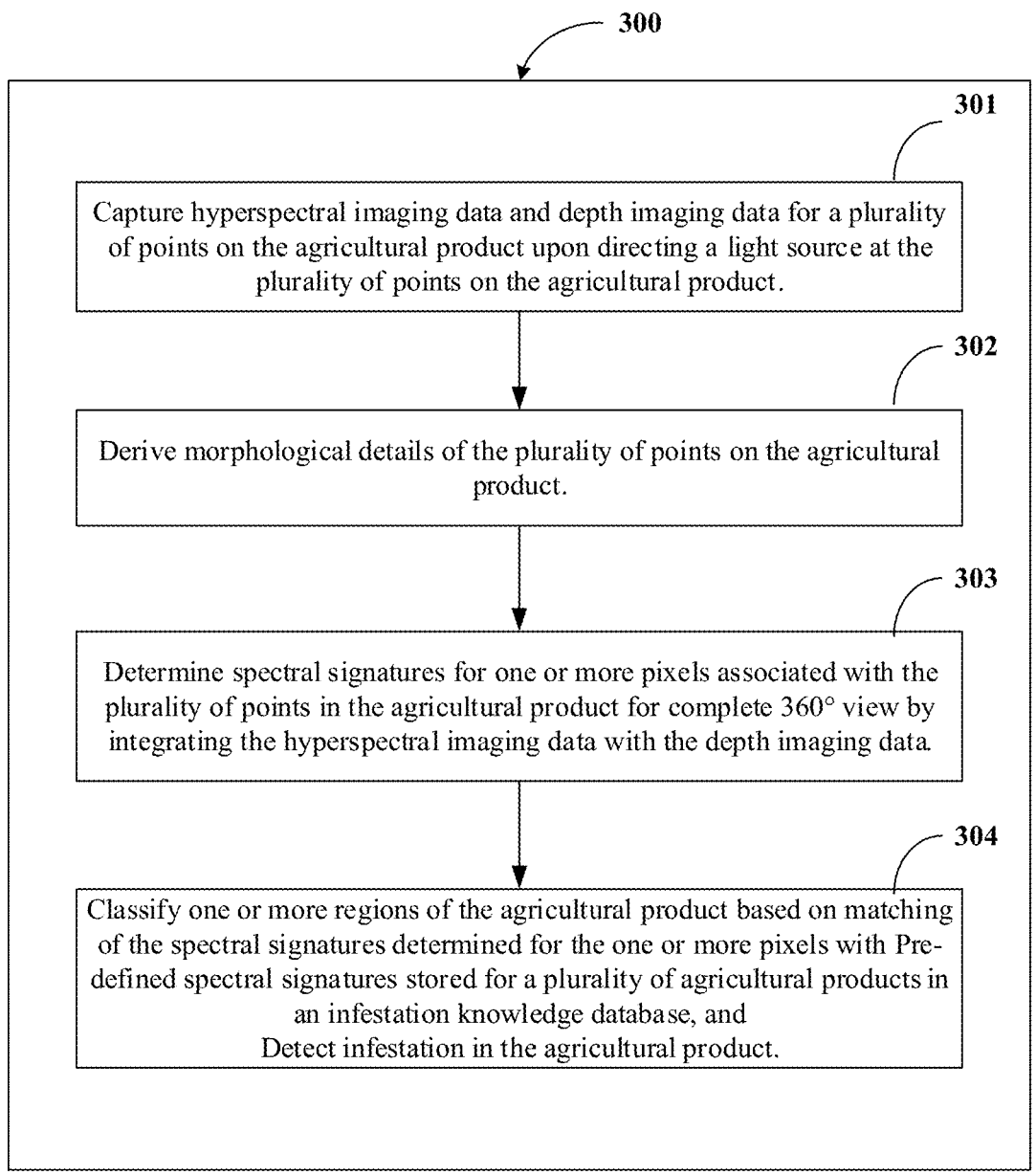
FIG. 3 is a flow diagram illustrating a process overview of providing detecting infestation in an agricultural product, in accordance with some embodiments of the present disclosure.

Referring now to FIG. 3, a flow diagram illustrating a process overview of detecting infestation in an agricultural product is depicted, in accordance with some embodiments of the present disclosure. The agricultural products, after being harvested, tested and scrutinized for quality and infestation before packaging and transportation. As illustrated in the flowchart, a control logic 300, in order to inspect each of the one or more agricultural products 104, may include the step of capturing hyperspectral imaging data and depth imaging data for a plurality of points on the agricultural product upon directing a light source at the plurality of points on the agricultural product, at step 301. The control logic 300 may further include the step of deriving morphological details and spectral signatures for complete 360° view of the plurality of points on the agricultural product for storing in an infestation knowledge database, at step 302. The control logic 300 may further include the step of correcting spectrum for one or more pixels associated with the plurality of points in the agricultural product based on depth information associated with the one or more pixels and a transformation function derived by integrating the hyperspectral imaging data (HSI data) 236 with the depth imaging data 238, at step 303. The control logic 300 may further include the step of classifying one or more regions of the agricultural product based on matching of spectral signatures determined for the one or more pixels with pre-defined spectral signatures stored for a plurality of agricultural products, and thereby detecting infestation in the agricultural product, at step 304.

At step 301, each of the one or more agricultural products 104 is passed through the conveyor system so that the imaging data can be captured for a plurality of points on the agricultural product using integrated setup of the lighting system, the plurality of image sensors 112 and the one or more cameras for capturing imaging data in different modalities. The lighting system includes a light source for illuminating the agricultural product for proper capturing of image frames. Further, the integrated setup may synchronize the speed of the conveyor belt and the one or more cameras for capturing different modalities so as to capture imaging data for every pixels in one or more modalities in a common coordinate system. For example, at time t1 an agricultural product to be captured are in the view of HSI unit, the conveyor belt speed needs to be tuned so as to place the same view of the agricultural product under the LIDAR sensor capturing region at time t2. Such synchronization facilitates in the mapping of the HSI data captured from HSI unit with the point cloud features captured using LIDAR sensor, thereby providing a type of 3-dimensional HSI data, which will be furthered for next modalities to generate comprehensive imaging data.

At step 302, the imaging data captured for different modalities is analyzed for deriving morphological details and spectral signatures for the plurality of points comprising 360° view of the agricultural product. In an embodiment, the imaging data from different modalities is fused in order to get improved morphological details and spectrum data for each of the plurality of points for complete 360° view of the agricultural product. Further, the imaging data captured from different modalities is fused together so to obtain refined spectral signatures that might not be accurate when obtained from single modality. For example, the hyperspectral image might suffer loss of reflectance due to irregular shape or curves at the surface of the agricultural product. Similarly, any infestation, if present at inner region of the agricultural product cannot be captured by existing sensing techniques such as RGB camera, HSI camera individually.

Figure 4:
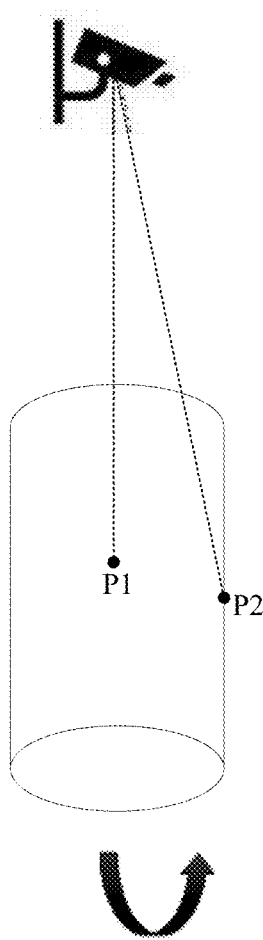
FIG. 4 illustrates an embodiment of spectral correction for the one or more pixels associated with an agricultural product, in accordance with an embodiment of the present disclosure.

Generally, when a light is transmitted on the agricultural product, there is loss of reflectance due to morphological irregularities on the edges of the agricultural product as shown in FIG. 4. The morphological irregularities in the agricultural product may include, but not limited to, depression, spine hole and the like. The light reflection loss from the edges and other morphological regions of the agricultural product results in incorrect values in imaging data, which can be corrected using angular orientation of the pixel captured using camera associated with the HSI unit. Therefore, the proposed method focusses on correcting the morphological details by correcting spectrum for each of the plurality of pixels for a plurality of points on the agricultural product. In order to identify infestation correctly, the proposed method and system derive imaging data of various regions of the agricultural product, perform correction in spectrum data upon determining loss in the light intensity in certain regions of the agricultural product, as explained below.

At step 303, in order to make necessary correction in spectrum for one or more pixels associated with the plurality of points in the agricultural product, the proposed infestation detection system uses depth information associated with the one or more pixels and a transformation function derived by integrating the HSI data 236 with the depth imaging data 238. The transformation function is derived to measure the change in intensity over change in the angle between the top plane of the agricultural product with any other point in the image. The transformation function is computed by determining loss of reflectance based on angular orientation of the one or more pixels captured in the camera associated with HSI unit.

FIG. 4 illustrates the embodiment of spectral correction for the one or more pixels associated with the agricultural product, in accordance with an embodiment of the present disclosure. As illustrated above, the imaging data captured using the plurality of image sensors 112 is analyzed to derive morphological details and spectral signatures associated with plurality of points in the agricultural product. The spectral signatures are captured for complete 360° view i.e. every angle for each of the plurality of points by rotating the agricultural product by pre-defined theta ($\Theta$) angle at a time. This will create N number of hyper cubes, wherein N=360/$\Theta$ for spectral signatures for the plurality of points in the agricultural product.

As shown in FIG. 4, points P1 and P2 is calculated for same class, so ideally they points P1 and P2 should have the same signatures. However, it is possible that point P2 gives a different signature due to change in spatial position of P2 in the agricultural product. Based on rotation of the agricultural product, when point P2 comes to the top plane and another spectral signature P2' is derived based on imaging data. Therefore, based on comparison of the two different signatures for point P2, change in intensity can be observed in spectrum based on change in angle.

The change in intensity in the spectrum upon change in angle is represented as:

$$\frac{\delta(\text{reflected intensity})}{\delta(\text{angle between P2 and P2}')} \quad \text{equation (1)}$$

The similar relation will hold true for other plurality of points in the agricultural product. Based on which, the transformation function can be computed for various angles for variety of categories of agricultural product based on type, sizes, quality and the like. The transformation function can be computed and stored in an infestation knowledge database, which can be used to correct the spectrum during inspection of the one or more agricultural products 104 in real-time.

Considering the two points in FIG. 5: point P1 (in the top plane defined as a reference point using the depth imaging data) that has a proper reflectance spectrum without any loss and point P2 (towards the edge) has an improper reflectance spectrum with loss. In such case, in order to rectify spectral signature for point P2 at the edge of the fruit, the spectral correction unit 228 uses the transformation function for point P2 signature by adjusting the reflectance spectrum to make the spectrum proper. In the embodiment, the proposed method corrects the spectrum for the one or more pixels by using the angle mapped data obtained from the Depth-Angle Mapper 226 and the transformation function taken from the infestation knowledge database 106, denoted as f (θ, spectrum)=$\vec{P}$, wherein $\vec{P}$ is the corrected spectrum.

FIG. 5 illustrates an embodiment of an infestation detection system having morphological segmentation details associated with a plurality of agricultural products, in accordance with some embodiments of the present disclosure. The infestation knowledge database 106 may store the details regarding the morphological classes of the agricultural product and respective spectral signatures. The morphological classes may include, but not limited to, curvy, edges, and valleys regions in the agricultural product. In order to compute depth-angle value for spectral correction, the HSI data may be pre-processed and applied with noise correction to create a correct hypercube. Herein, the depth imaging data may be processed to individually extract data for various regions of morphological segments such as curve, edge, valley and the like as channel 1, channel 2, channel N of the agricultural product. Each morphological segmentation details will exhibit a different signature for each physical class (such as infested, fresh and the like) along with the signature that it would have shown in an ideal scenario with no loss in spectrum. A hypercube created from the HSI data 236 may be divided into N data-cubes. In an embodiment, various regions of morphological segments extracted from the depth imaging data 238 may be used to divide the hypercube into N data-cubes.

Accordingly, the infestation detection system 102 may classify each of the N data-cubes using the spectral signatures pre-defined for the morphological segments such as infested, fresh and the like. Based on classification, the intelligent decision engine 232 may provide results for infestation detection for the agricultural product in accordance with the embodiment.

Referring back to FIG. 3, at step 304, the intelligent decision engine 232 classifies the agricultural product based on infestation. In an embodiment, the intelligent decision engine 232 may utilizes and the plurality of data-cubes collected for the one or more pixels covering the complete 360° view of the agricultural product. In an embodiment, the intelligent decision engine 232 implements a heuristic approach over plurality of data-cubes to determine infestation in various regions of the agricultural product. In an embodiment, the infestation detection system 102 upon identifying infestation in one or more regions of the agricultural product may further classify the agricultural product into fresh or bad quality by the help of a segregation unit (not shown in FIG. 2).

In an embodiment, the infestation detection system 102 may take into consideration various regions comprising entire surface of the agricultural product in order to decide whether the agricultural product is infested or not. In an embodiment, the infestation detection system 102 it may pre-defined threshold values decided for degree of infestation. In some embodiments, it also takes into consideration the imaging data obtained from different modalities. For example, the X-Ray images may be used in addition to determine infestation at inner regions of the agricultural product. The consideration of the imaging data from different modalities and its effect on the physical classes results in output based on fused data.

In addition to above, the segregation unit takes input from the intelligent decision engine 232 and may guide an agent to separate the agricultural product which is of good quality from an agricultural product of bad quality. In an embodiment, the segregation unit may send the agriculture product for further inspection in case of no outcome, which may arise due to some issues such as improper data collection. In some embodiments, the segregation unit may implement the decision of intelligent decision engine 232 by using robotic arms or air-cannon which distinguishing one class from other. Thereafter, the good quality agricultural product can be proceeded for further processing or packaging.

As will be also appreciated, the above described techniques may take the form of computer or controller implemented processes and apparatuses for practicing those processes. The disclosure can also be embodied in the form of computer program code containing instructions embodied in tangible media, such as floppy diskettes, solid state drives, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Figure 6:
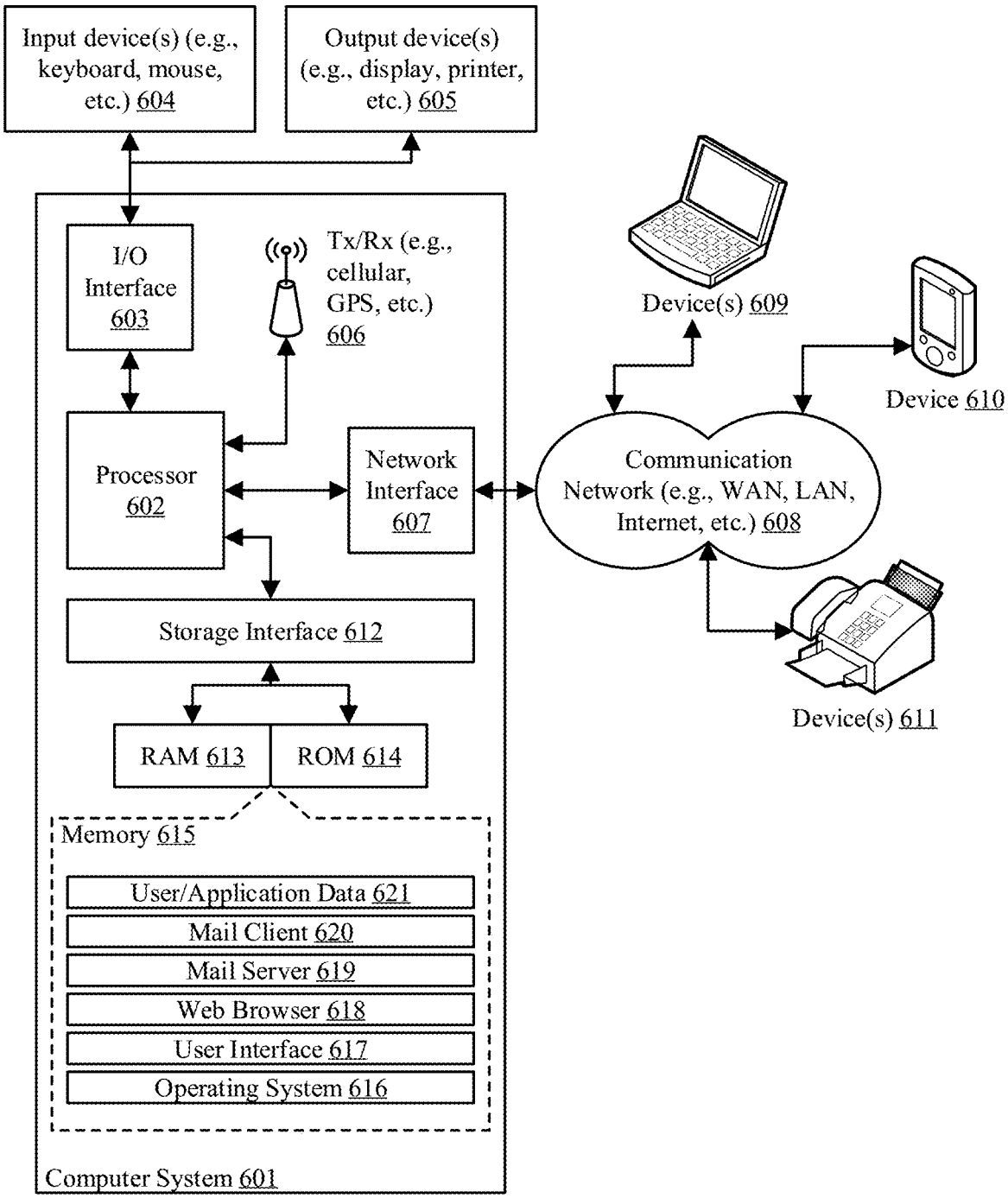
FIG. 6 is a block diagram of an exemplary computer system for implementing embodiments consistent with the present disclosure.

FIG. 6 is a block diagram of an exemplary computer system for implementing embodiments consistent with the present disclosure. Variations of computer system 601 may be used for implementing list all computers from other figures. Computer system 601 may comprise a central processing unit ("CPU" or "processor") 602. Processor 602 may comprise at least one data processor for executing program components for executing user- or system-generated requests. A user may include a person, a person using a device such as such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 602 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 602 may be disposed in communication with one or more input/output (I/O) devices via I/O interface 603. The I/O interface 603 may employ communication protocols/methods such as, without limitation, audio, analog, digital, monoaural, RCA, stereo, IEEE-1396, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 603, the computer system 601 may communicate with one or more I/O devices. For example, the input device 604 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 605 may be a printer, fax machine, video display (e.g., cathode ray tube (CRT), liquid crystal display (LCD), light-emitting diode (LED), plasma, or the like), audio speaker, etc. In some embodiments, a transceiver 606 may be disposed in connection with the processor 602. The transceiver may facilitate various types of wireless transmission or reception. For example, the transceiver may include an antenna operatively connected to a transceiver chip (e.g., Texas Instruments WiLink WL1283, Broadcom BCM6760IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 602 may be disposed in communication with a communication network 608 via a network interface 607. The network interface 607 may communicate with the communication network 608. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 608 may include, without limitation, a direct interconnection, local area network (LAN), wide area network (WAN), wireless network (e.g., using Wireless Application Protocol), the Internet, etc. Using the network interface 607 and the communication network 608, the computer system 601 may communicate with devices 609, 610, and 611. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 601 may itself embody one or more of these devices.

In some embodiments, the processor 602 may be disposed in communication with one or more memory devices (e.g., RAM 613, ROM 614, etc.) via a storage interface 612. The storage interface may connect to memory devices 615 including, without limitation, memory drives, removable disc drives, etc., employing connection protocols such as serial advanced technology attachment (SATA), integrated drive electronics (IDE), IEEE-1396, universal serial bus (USB), fiber channel, small computer systems interface (SCSI), etc. The memory drives 616 may further include a drum, magnetic disc drive, magneto-optical drive, optical drive, redundant array of independent discs (RAID), solid-state memory devices, solid-state drives, etc.

The memory devices 615 may store a collection of program or database components, including, without limitation, an operating system 616, user interface application 617, web browser 618, mail server 619, mail client 620, user/application data 621 (e.g., any data variables or data records discussed in this disclosure), etc. The operating system 616 may facilitate resource management and operation of the computer system 601. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 617 may facilitate display, execution, interaction, manipulation, or operation of program components through textual or graphical facilities. For example, user interfaces may provide computer interaction interface elements on a display system operatively connected to the computer system 601, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 601 may implement a web browser 618 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 601 may implement a mail server 619 stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 601 may implement a mail client 620 stored program component. The mail client may be a mail viewing application, such as Apple Mail, Microsoft Entourage, Microsoft Outlook, Mozilla Thunderbird, etc.

In some embodiments, computer system 601 may store user/application data 621, such as the data, variables, records, etc. (e.g., list here) as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

The specification has described method and system for detecting infestation in agricultural products. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

Advantages of the Present Disclosure.

Present system and method provides a non-destructive infestation detection techniques for accurate detection of morphological details of the plurality of agricultural products and error-free classification of the agricultural products in timely manner. The proposed technique can be easily integrated into the existing industrial setup.

Further the proposed integrated method combines data from Hyper Spectral Imaging, Depth Imaging & X-ray Imaging to get the composite data with image registration for the accurate infestation detection. Further, the infestation detection system derives angular orientation information for each pixel in the composite data based on proposed method. Further it combines multiple composite data to cover the entire surface of the fruit and make the intelligent decision to decide whether a particular fruit is to be rejected or accepted. Also, it enables that the composite data can be segregated based on the morphological feature and can be processed independently.

Further, the present disclosure suggests use of machine learning technique for detection infestation using pre-trained data. The pre-trained trained data is based on integrated imaging data and provide correct spectral signatures for one or more regions of the agricultural product for classification and quicker detection of infestation in the agricultural product.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The specification has described a method and a system for detecting infestation in an agricultural product. The illustrated steps are set out to explain the exemplary embodiments shown, and it should be anticipated that on-going technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

We claim:

1. A method of detecting infestation in agricultural products, the method comprises:

capturing, by an infestation detection system, hyperspectral imaging data and depth imaging data for a plurality of points on an agricultural product upon directing a light source at the plurality of points on the agricultural product;

deriving, by the infestation detection system, morphological details for the plurality of points on the agricultural product;

determining, by the infestation detection system, spectral signatures for one or more pixels associated with the plurality of points in the agricultural product for complete 360° view by integrating the hyperspectral imaging data with the depth imaging data, wherein determining the spectral signatures further comprises:

correcting spectrum for one or more pixels associated with the plurality of points in the agricultural product based on depth information associated with the one or more pixels and a transformation function computed by integrating the hyperspectral imaging data with the depth imaging data, wherein the transformation function is computed for the plurality of points based on change in intensity over change in angle between a first point at top plane of the agricultural product to a second at any other region than top plane of the agricultural product; and classifying, by the infestation detection system, one or more regions of the agricultural product based on matching of the spectral signatures determined for the one or more pixels with pre-defined spectral signatures stored for a plurality of agricultural products in an infestation knowledge database, and thereby detecting the infestation in the agricultural product.

2. The method as claimed in claim 1 further comprises segregating the agricultural product into at least one of fresh, infested or severely damaged based on the infestation detected in the one or more regions of the agricultural product using the spectral signatures.

3. The method as claimed in claim 1, wherein classifying the one or more regions of the agricultural product further comprises:

identifying one or more morphological regions in the agricultural product using a pre-trained model;

deriving the spectral signatures by integrating the depth imaging data with corresponding hyperspectral imaging data for the one or more morphological regions; and detecting the infestation for the one or more morphological regions in the agricultural product.

4. The method as claimed in claim 1, wherein the hyperspectral imaging data comprises spectral information associated with one or more pixels obtained using hyperspectral imaging in the form of hyperspectral cubes for one or more pixels in the agricultural product; and wherein the depth imaging data comprises depth information for one or more pixels associated with the one or more regions in the agricultural product obtained using depth sensor.

5. The method as claimed in claim 1, wherein detecting the infestation in the agricultural product further comprises determining at least one of a type of the agricultural product and associated one or more disease type, stages of infestation, severity of damages, presence of pathogens, presence of harmful residues, survival life of the agricultural product, probable treatment against infestation.

6. The method as claimed in claim 1, wherein detecting the infestation in the agricultural product further comprises detecting internal damage in the agricultural product using x-ray imaging data.

7. An infestation detection system for agricultural products, the infestation detection system comprises:

a plurality of image sensors;

at least one processor;

a memory communicatively coupled to the at least one processor, wherein the memory stores the at least one processor-executable instructions, which, on execution, causes the at least one processor to:

capture hyperspectral imaging data and depth imaging data for a plurality of points on an agricultural product upon directing a light source at the plurality of points on the agricultural product;

derive morphological details for the plurality of points on the agricultural product;

determine spectral signatures for one or more pixels associated with the plurality of points in the agricultural product for complete 360° view by integrating the hyperspectral imaging data with the depth imaging data, wherein the at least one processor-executable instructions to determine the spectral signatures further causes the at least one processor-executable to:

correct spectrum for one or more pixels associated with the plurality of points in the agricultural product based on depth information associated with the one or more pixels and a transformation function computed by integrating the hyperspectral imaging data with the depth imaging data, wherein the transformation function is computed for the plurality of points based on change in intensity over change in angle between a first point at top plane of the agricultural product to a second at any other region than top plane of the agricultural product; and classify one or more regions of the agricultural product based on matching of spectral signatures determined for the one or more pixels with pre-defined spectral signatures stored for a plurality of agricultural products in an infestation knowledge database, and thereby detecting infestation in the agricultural product.

8. The infestation detection system as claimed in claim 7 further causes the at least one processor to segregate the agricultural product into at least one of fresh, infested or severely damaged based on the infestation detected in the one or more regions of the agricultural product using the spectral signatures.

9. The infestation detection system as claimed in claim 7, wherein the at least one processor-executable instructions to classify the one or more regions of the agricultural product further causes the at least one processor to:

identify one or more morphological regions in the agricultural product using a pre-trained model;

derive the spectral signatures by integrating the depth imaging data with corresponding hyperspectral imaging data for the one or more morphological regions: and detect the infestation for the one or more morphological regions in the agricultural product.

10. The infestation detection system as claimed in claim 7, wherein the hyperspectral imaging data comprises spectral information associated with one or more pixels obtained using hyperspectral imaging in the form of hyperspectral cubes for one or more pixels in the agricultural product; and wherein the depth imaging data comprises depth information for one or more pixels associated with the one or more regions in the agricultural product obtained using depth sensor.

11. The infestation detection system as claimed in claim 7, wherein the at least one processor-executable instructions to detect infestation in the agricultural product further causes the at least one processor to determine at least one of a type of the agricultural product and associated one or more disease types, stages of infestation, severity of damages, presence of pathogens, presence of harmful residues, survival life of the agricultural product, probable treatment against infestation.

12. The infestation detection system as claimed in claim 7, wherein the at least one processor-executable instructions to detect infestation in the agricultural product further causes the at least one processor to detect internal damage in the agricultural product using x-ray imaging data.

13. A non-transitory computer-readable medium having stored thereon a set of computer-executable instructions for detecting infestation in agricultural products, the set of computer-executable instructions causing a computer comprising one or more processors to perform steps comprising:

capturing, by an infestation detection system, hyperspectral imaging data and depth imaging data for a plurality of points on an agricultural product upon directing a light source at the plurality of points on the agricultural product;

deriving, by the infestation detection system, morphological details for the plurality of points on the agricultural product;

determining, by the infestation detection system, spectral signatures for one or more pixels associated with the plurality of points in the agricultural product for complete 360° view by integrating the hyperspectral imaging data with the depth imaging data, wherein determining the spectral signatures further comprises:

correcting spectrum for one or more pixels associated with the plurality of points in the agricultural product based on depth information associated with the one or more pixels and a transformation function computed by integrating the hyperspectral imaging data with the depth imaging data, wherein the transformation function is computed for the plurality of points based on change in intensity over change in angle between a first point at top plane of the agricultural product to a second at any other region than top plane of the agricultural product; and classifying, by the infestation detection system, one or more regions of the agricultural product based on matching of the spectral signatures determined for the one or more pixels with pre-defined spectral signatures stored for a plurality of agricultural products in an infestation knowledge database, and thereby detecting the infestation in the agricultural product.

14. The non-transitory computer-readable medium of claim 13, wherein the steps further comprise segregating the agricultural product into at least one of fresh, infested or severely damaged based on the infestation detected in the one or more regions of the agricultural product using the spectral signatures.

15. The non-transitory computer-readable medium of claim 13, wherein classifying the one or more regions of the agricultural product further comprises:

identifying one or more morphological regions in the agricultural product using a pre-trained model;

deriving the spectral signatures by integrating the depth imaging data with corresponding hyperspectral imaging data for the one or more morphological regions; and detecting the infestation for the one or more morphological regions in the agricultural product.

16. The non-transitory computer-readable medium of claim 13, wherein the steps for detecting infestation in the agricultural product further comprise determining at least one of a type of the agricultural product and associated one or more disease type, stages of infestation, severity of damages, presence of pathogens, presence of harmful residues, survival life of the agricultural product, probable treatment against infestation.

17. The non-transitory computer-readable medium of claim 13, wherein the steps for detecting infestation in the agricultural product further comprise detecting internal damage in the agricultural product using x-ray imaging data.

* * * * *